US00RE47604E

(19) United States
(12) Reissued Patent
Miyazaki

(10) Patent Number: US RE47,604 E
(45) Date of Reissued Patent: *Sep. 17, 2019

(54) MAGNETIC RESONANCE IMAGING APPARATUS AND METHOD FOR COLOR-CODING TISSUE BASED ON T1 VALUES

(71) Applicant: TOSHIBA MEDICAL SYSTEMS CORPORATION, Otawara-shi, Tochigi (JP)

(72) Inventor: Mitsue Miyazaki, Des Plaines, IL (US)

(73) Assignee: TOSHIBA MEDICAL SYSTEMS CORPORATION, Otawara-Shi, Tochigi (JP)

( * ) Notice: This patent is subject to a terminal disclaimer.

(21) Appl. No.: 15/793,564

(22) Filed: Oct. 25, 2017

Related U.S. Patent Documents

Reissue of:
(64) Patent No.: 9,167,988
Issued: Oct. 27, 2015
Appl. No.: 13/649,636
Filed: Oct. 11, 2012

U.S. Applications:
(63) Continuation-in-part of application No. 12/923,891, filed on Oct. 13, 2010, now Pat. No. 10,267,882.

(30) Foreign Application Priority Data

Oct. 13, 2011 (JP) ..... 2011-226172

(51) Int. Cl.
*A61B 5/05* (2006.01)
*A61B 5/055* (2006.01)
(Continued)

(52) U.S. Cl.
CPC ..... *A61B 5/055* (2013.01); *A61B 5/742* (2013.01); *A61B 5/7425* (2013.01); *A61M 5/007* (2013.01); *G01R 33/5608* (2013.01); *G01R 33/50* (2013.01)

(58) Field of Classification Search
CPC ..... A61B 5/055; A61B 5/742; A61B 5/7425; A61M 5/007; G01R 33/5608; G01R 33/50
See application file for complete search history.

(56) References Cited

U.S. PATENT DOCUMENTS 3,789,832 A 2/1974 Damadian
4,698,593 A 10/1987 Crooks
(Continued)

FOREIGN PATENT DOCUMENTS

CN 1973211 A 5/2007
JP 2000-166897 6/2000
(Continued)

OTHER PUBLICATIONS

International Search Report dated Dec. 20, 2011 in PCT/JP2011/073570.
(Continued)

*Primary Examiner* — Jeffrey R Jastrzab
(74) *Attorney, Agent, or Firm* — Nixon & Vanderhye P.C.

(57) ABSTRACT

A magnetic resonance imaging apparatus according to an exemplary embodiment includes a memory, a specifying unit, and a display controller. The memory stores a corresponding color table representing correspondence relationships between T1 values of which value ranges with respect to each tissue are known and colors to be assigned to pixels with the T1 values. The specifying unit analyzes a T1-valued image and specifies colors to be assigned to each pixel on the basis of T1 values converted from pixel values of each pixel and the corresponding color table. The display controller displays on a display the image color-coded with the specified colors.

25 Claims, 3 Drawing Sheets

(51) Int. Cl.

| | |
|---|---|
| ***G01R 33/56*** | (2006.01) |
| ***A61B 5/00*** | (2006.01) |
| ***A61M 5/00*** | (2006.01) |
| *G01R 33/50* | (2006.01) |

(56) References Cited

U.S. PATENT DOCUMENTS

| | | | | |
|---|---|---|---|---|
| 5,332,968 | A * | 7/1994 | Brown | 324/309 |
| 6,009,342 | A | 12/1999 | Brasch et al. | |
| 6,674,880 | B1 | 1/2004 | Stork et al. | |
| 6,804,384 | B2 | 10/2004 | Lowen | |
| 7,155,043 | B2 | 12/2006 | Daw | |
| 2003/0095147 | A1* | 5/2003 | Daw | 345/771 |
| 2005/0190955 | A1 | 9/2005 | Brown | |
| 2006/0273790 | A1 | 12/2006 | Eggers et al. | |
| 2008/0004519 | A1* | 1/2008 | Theriault | A61B 5/055 600/410 |
| 2008/0012563 | A1 | 1/2008 | Weiss et al. | |
| 2008/0150532 | A1 | 6/2008 | Slavin et al. | |
| 2008/0300482 | A1 | 12/2008 | Mlejnek et al. | |
| 2009/0232410 | A1 | 9/2009 | Dahnke et al. | |
| 2010/0103166 | A1 | 4/2010 | Warntjes | |

FOREIGN PATENT DOCUMENTS

| | | |
|---|---|---|
| JP | 2003-325510 | 11/2003 |
| JP | 2006-524084 | 10/2006 |
| JP | 2007-536970 | 12/2007 |
| JP | 2008-534044 | 8/2008 |
| JP | 2009-512932 | 3/2009 |
| JP | 2010-075549 | 4/2010 |

OTHER PUBLICATIONS

Office Action dated Jun. 23, 2015 in JP Patent Application No. 2011-226172.

Extended European Search Report dated Mar. 29, 2017 in EP 11832601.6.

Office Action dated Jul. 18, 2017 in JP Patent Application No. 2011-226172.

Kamman et al., "Unified Multiple-Feature Color Display for MR Images", Magnetic Resonance in Medicine, vol. 9, Issue 2, (1989), pp. 240-253.

Fantazzini et al., "Use of Magnetic Resonance Imaging for monitoring Parma dry-cured ham processing," Meat Science, Elsevier Science, GB, vol. 82, No. 2, Jun. 1, 2009, pp. 219-227.

Vrenken et al., "Voxel-Based Analysis of Quantitative T1 Maps Demonstrates That Multiple Sclerosis Acts throughout the Normal-Appearing White Matter," American Journal of Neuroradiology, vol. 27, Apr. 1, 2006, pp. 868-874.

Liu et al., "Multi-spectral Analysis of Relaxation Time Maps on Fetal Baboon Brains," Proceedings of the International Society for Magnetic Resonance in Medicine, ISMRM, 16th Scientific Meeting and Exhibition, Toronto, Canada, May 3-9, 2008, Apr. 19, 2008, p. 3378.

Alfano et al., "Evaluation of brain tumors using the R1, R2, PD domain," Proceedings of the International Society for Magnetic Resonance in Medicine, ISMRM, Twelfth Annual Scientific Meeting Aug. 14-20, 1993, New York, New York, USA, Aug. 14, 1993, p. 1468.

Final Office Action dated Aug. 3, 2018 in counterpart U.S. Appl. No. 12/923,891.

Kamman, R. L. et al., "Unified Multiple-Feature Color Display for MR Images", Magnetic Resonance in Medicine 9, (1989), pp. 240-253.

Scheffler, Klaus et al.,"T1 Quantification With Inversion Recovery TrueFISP", Magnetic Resonance in Medicine 45: (2001), pp. 720-723.

Kuhl, et al., "Dynamic Breast MR Imaging: Are Signal Intensity Time Course Data Useful for Differential Diagnosis of Enhancing Lesions?," Radiology, vol. 211, No. 1, pp. 101-110 (Apr. 1999).

Kuhl, "The Current Status of Breast MR Imaging, Part I, Choice of Technique, Image Interpretation, Diagnostic Accuracy, and Transfer to Clinical Practice," Radiology, vol. 244, No. 2, pp. 356-378 (Aug. 2007).

Kuhl, "Current Status of Breast MR Imaging, Part 2, Clinical Applications," Radiology, vol. 244, No. 3, pp. 672-691 (Sep. 2007).

Breger, et al., "T1 and T2 Measurements on a 1.5-T Commercial MR Imager," Radiology, vol. 171, No. 1, pp. 273-276 (Apr. 1989).

De Bazelaire, et al., "MR Imaging Relaxation Times of Abdominal and Pelvic Tissues Measured in Vivo at 3.0 T: Preliminary Results," Radiology, vol. 230, No. 3, pp. 652-659 (Mar. 2004).

Stanisz, et al., "$T_1$, $T_2$ Relaxation and Magnetization Transfer in Tissue at 3T," Magnetic Resonance in Medicine, vol. 54, pp. 507-512 (2005).

Office Action dated Dec. 17, 2012 in U.S. Appl. No. 12/923,891.

Office Action dated Dec. 18, 2013 in Chinese Application No. 201180003911.4.

* cited by examiner

MAGNETIC RESONANCE IMAGING APPARATUS AND METHOD FOR COLOR-CODING TISSUE BASED ON T1 VALUES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a continuation-in-part (CIP) of application Ser. No. 12/923,891 filed Oct. 13, 2010, the entire content of which is hereby incorporated by reference in this application. This application is based upon and claims the benefit of priority from Japanese Patent Application No. 2011-226172, filed on Oct. 13, 2011, the entire contents of all of which are incorporated herein by reference.

FIELD

Exemplary embodiments relate to a magnetic resonance imaging apparatus, a magnetic resonance imaging method and an image display apparatus.

BACKGROUND

In imaging performed by conventional magnetic resonance imaging apparatuses (hereinafter, MRI (magnetic resonance imaging) system), T1-weighted images for which T1 denoting a longitudinal relaxation time is weighted or T2-weighted images for which T2 denoting a transverse relaxation time is weighted are collected by changing imaging conditions of a pulse sequence.

DETAILED DESCRIPTION

A magnetic resonance imaging apparatus according to an exemplary embodiment includes a memory, a specifying unit, and a display controller. The memory stores a corresponding color table representing correspondence relationships between T1 values of which value ranges with respect to each tissue are known and colors to be assigned to pixels with the T1 values. The specifying unit analyzes a T1-valued image and specifies colors to be assigned to each pixel on the basis of T1 values converted from pixel values of each pixel and the corresponding color table. The display controller displays on a display the image color-coded with the specified colors.

Figure 1:
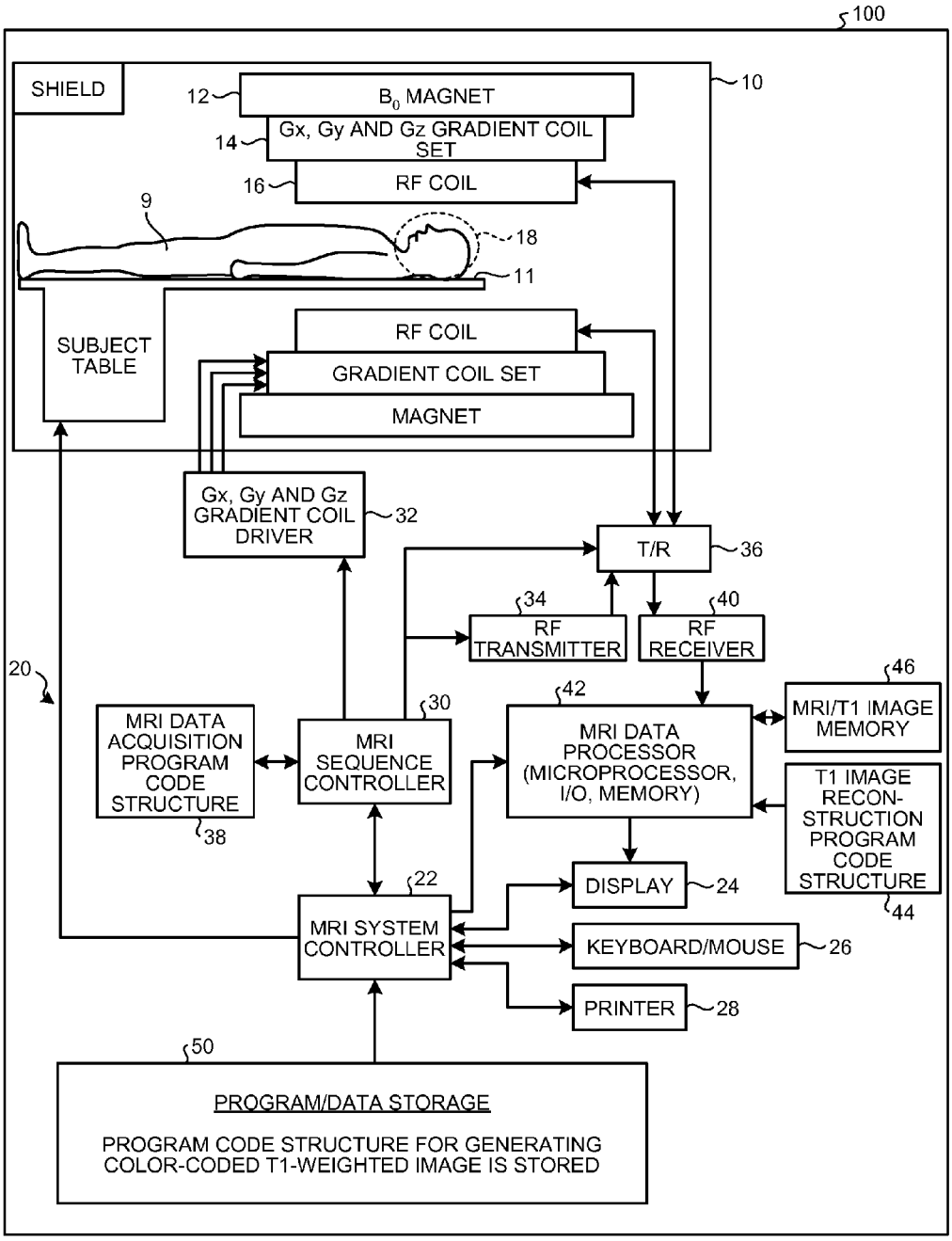
FIG. 1 is a schematic block diagram of an MRI system according to an exemplary embodiment.

An MRI (magnetic resonance imaging) system 100 shown in FIG. 1 includes a gantry 10 (shown in cross-section) and various related system components 20 interfaced therewith. At least the gantry 10 is typically located in a shielded room. One MRI system 100 depicted in FIG. 1 includes a substantially coaxial cylindrical arrangement of the static field $B_0$ magnet 12, a $G_x$, $G_y$ and $G_z$ gradient coil set 14 and an RF (radio frequency) coil assembly 16. Along the horizontal axis of the components cylindrically arranged, there is an imaging volume 18 shown as encompassing the head of a subject 9 supported by a subject table 11.

An MRI system controller 22 has input/output ports connected to a display 24, a keyboard/mouse 26 and a printer 28. As will be appreciated, the display 24 may be of the touchscreen variety so that it provides control inputs as well.

The MRI system controller 22 interfaces with an MRI sequence controller 30. The MRI sequence controller 30 sequentially controls G.sub.x, G.sub.y and G.sub.z gradient coil drivers 32, as well as an RF transmitter 34 and a transmit/receive switch 36 (if the same RF coil is used for both transmission and reception). The MRI sequence controller 30 includes a suitable program code structure 38 for implementing MRI data acquisition sequences available in the MRI sequence controller 30 to collect T1-valued images (for example, by collecting a plurality of MR images collected at different TR (repetition time values)).

The MRI system 100 includes an RF receiver 40 providing input to an MRI data processor 42 so as to create processed image data to be output to the display 24. The MRI data processor 42 may be also configured to access an image reconstruction program code structure 44 and an MR image memory 46 (e.g., for storing T1-valued MR images derived from processing in accordance with the exemplary embodiments and the image reconstruction program code structure 44).

FIG. 1 also gives a generalized depiction of an MRI system program/data storage 50. The program code structures (e.g., for generation of color-coded T1-images, operator inputs to the generation, etc.) stored in the MRI system program/data storage 50 are stored in computer-readable storage media accessible to the various data processing components of the MRI system 100. As those in the art will appreciate, the MRI system program/data storage 50 may be segmented and directly connected, at least in part, to different ones of processing computers of the system having most immediate need for such stored program code structures in their normal operation (i.e., rather than being commonly stored in and connected directly to the MRI system controller 22).

Indeed, as those in the art will appreciate, the depiction of FIG. 1 is of a very high-level simplified diagram of the typical MRI system 100 with some modifications so as to practice the exemplary embodiments to be described below. The system components can be divided into different logical collections of "boxes" and typically include numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs (central processing units), registers, buffers, arithmetic units, etc.) progressively change from one clock cycle to another during the operation, the physical state of associated data storage media (e.g., bit storage sites in magnetic storage media) is transformed from one state to another during operation of such a system. For example, at the conclusion of an MR-imaging reconstruction process, an array of computer-readable accessible data value storage in physical storage media will be transformed from some prior state (e.g., all uniform "zero" values or all "one" values) to a new state. In such a new state, the physical states at the physical sites of such an array vary between minimum and maximum values to represent real world physical events and conditions (e.g., the tissues of a subject over an imaging volume space). As those in the art will appreciate, such arrays of stored data values represent and also constitute a physical structure. In other words, when program code instructions are sequentially loaded into instruction registers and executed by one or more CPUs of the MRI system 100, a particular sequence of operational states occurs and a particular structure of computer control program codes transitioned through within the MRI system 100 is configured.

The exemplary embodiments described below provide improved ways to process data acquisitions and/or to generate and display MR-images.

By analyzing a T1-valued image, the MRI system 100 according to exemplary embodiments assigns each pixel in the image colors and displays the color-coded image on the display. Note that "T1" denotes a relaxation time regarding magnetization recovery on the z-axis. In addition, "T1 -valued image" includes "T1 image" and "T1-weighted image". A "T1 image" is an image of ideal values that is collected by using TR (repetition time) 5 times larger than T1 and that is not affected by T2. In contrast, a "T1 weighted image" is a T1-value signal-intensity increased image that is collected by using a TR shorter than the five-fold TR. For example, usually, regarding a "T1 weighted image", a TR is short (e.g., 500 msec or less) and a TE (echo time) is short as well. The MRI system 100 according to the exemplary embodiment will be described as one using a "T1 weighted image" as a "T1-valued image" but the MRI system 100 is not limited to this, and it can be similarly applied to a case where a "T1 image" is used. Exemplary embodiments are not limited to the following also with respect to other aspects.

An exemplary embodiment will be described using specific examples. Even if contrast materials are injected into a subject's anatomy, thus increased MR signals may still be missed when the image is used for diagnostic purposes. However, as may be ascertained from Table 1 (mean T1 relaxation time using both 1.5 Tesla and 3.0 Tesla), it can be expected that different tissues (hereinafter, a tissue and/or organ is referred to as "tissue" as appropriate) have different T1-value ranges for 1.5 Tesla and 3.0 Tesla parameters. In contrast, as can be ascertained from Table 2 (mean T2 relaxation time using both 1.5 Tesla and 3.0 Tesla), T2 values are relatively similar with partly overlapping ranges that make it difficult to differentiate. For this reason, the MRI system 100 according to the following exemplary embodiment uses a method of assigning colors according to the T1-value ranges. However, exemplary embodiments are not limited to this. For example, a method may be used in which a T2-weighted image is collected and colors are assigned in accordance with T2-value ranges. Alternatively, a method may be used in which colors are assigned by, for example, selectively using both T1 values and T2 values.

The following tables are taken from de Bazelaire, et al., "MR Imaging Relaxation Times of Abdominal and Pelvic Tissues Measured in Vivo at 3.0T," Radiology 230:3, pages 652-659, March 2004. As those in the art will appreciate, there are other sources of similar data readily available in the literature. For example, see Stanisz, et al, "T1, T2 Relaxation and Magnetization Transfer in Tissue at 3T," MRIM 54:507-512 (2005).

TABLE 1

| | 1.5 Tesla | | 3.0 Tesla | | |
|---|---|---|---|---|---|
| Tissue | T1 Relaxation Time (msec) | $R^2$ Value (%) | T1 Relaxation Time (msec) | $R^2$ Value (%) | Difference (%) |
| Kidney | | | | | |
| Cortex | 966 ± 58 | 0.999 | 1,142 ± 154 | 0.990 | 18 |
| Medulla | 1,412 ± 58 | 0.997 | 1,545 ± 142 | 0.999 | 9 |
| Liver | 586 ± 39 | 0.995 | 809 ± 71 | 0.987 | 38 |
| Spleen | 1,057 ± 42 | 0.998 | 1,328 ± 31 | 0.998 | 26 |
| Pancreas | 584 ± 14 | 0.982 | 725 ± 71 | 0.976 | 24 |
| Paravertebral muscle | 856 ± 61 | 0.988 | 898 ± 33 | 0.988 | 5 |
| Bone marrow (L4 vertebra) | 549 ± 52 | 0.991 | 586 ± 73 | 0.994 | 7 |
| Subcutaneous fat | 343 ± 37 | 0.997 | 382 ± 13 | 0.999 | 11 |
| Uterus | | | | | |
| Myometrium | 1,309 ± 35 | 0.998 | 1,514 ± 156 | 0.999 | 16 |
| Endometrium | 1,274 ± 64 | 0.997 | 1,453 ± 123 | 0.998 | 14 |
| Cervix | 1,135 ± 154 | 0.998 | 1,616 ± 61 | 0.998 | 42 |
| Prostate | 1,317 ± 85 | 0.999 | 1,597 ± 42 | 0.998 | 21 |

TABLE 2

| | 1.5 Tesla | | 3.0 Tesla | | |
|---|---|---|---|---|---|
| Tissue | T1 Relaxation Time (msec) | $R^2$ Value (%) | T1 Relaxation Time (msec) | $R^2$ Value (%) | Difference (%) |
| Kidney | | | | | |
| Cortex | 87 ± 4 | 0.993 | 76 ± 7 | 0.993 | −13 |
| Medulla | 85 ± 11 | 0.992 | 81 ± 8 | 0.996 | −5 |
| Liver | 46 ± 6 | 0.992 | 34 ± 4 | 0.984 | −26 |
| Spleen | 79 ± 15 | 0.998 | 61 ± 9 | 0.996 | −23 |
| Pancreas | 46 ± 6 | 0.989 | 43 ± 7 | 0.977 | −7 |
| Paravertebral muscle | 27 ± 8 | 0.925 | 29 ± 4 | 0.867 | 7 |
| Bone marrow (L4 vertebra) | 49 ± 8 | 0.997 | 49 ± 4 | 0.994 | 1 |
| Subcutaneous fat | 58 ± 4 | 0.995 | 68 ± 4 | 0.999 | 17 |
| Uterus | | | | | |
| Myometrium | 117 ± 14 | 0.995 | 79 ± 10 | 0.993 | −33 |
| Endometrium | 101 ± 21 | 0.987 | 59 ± 1 | 0.999 | −42 |
| Cervix | 58 ± 20 | 0.993 | 83 ± 7 | 0.992 | 43 |
| Prostate | 88 ± 0 | 0.997 | 74 ± 9 | 0.995 | −16 |

The MRI system 100 according to the exemplary embodiment uses T1-weighted images to acquire improved CAD (computer aided diagnostic) images. Although the expression "CAD images" is taken in the sense that acquired images are used for diagnosis. However, the purpose is not limited to this and the acquired images may be used for any purpose (other than CAD). Furthermore, the MRI system 100 according to the exemplary embodiment is effective in a case where it is applied to intracranial MRA (magnetic resonance angiography) and body areas excluding breast tissues.

The exemplary embodiment described below uses a method in which T1 values are obtained by converting pixel values of each pixel contained in a T1-weighted image and colors to be assigned to each pixel are specified on the basis of obtained T1 values. Hereinafter, this method is referred to as "Pattern A". In addition, conversion of pixel values to T1 values is performed in this "Pattern A" and, hereinafter, a method of performing such conversion by analyzing a plurality of T1-weighted images under different imaging conditions is referred to as "Pattern A1" and a method of performing such conversion by using a corresponding value table representing correspondence relationships between pixel values and T1 values is referred to as "Pattern A2". There is another method, in one exemplary embodiment, of specifying colors to be assigned to each pixel on the basis of pixel values of each pixel contained in a T1-weighted image. Hereinafter, this method is referred to as "Pattern B". A T1-weighted image may be collected by the MRI system 100 or may be previously collected and input to the MRI system 100. A case in which a T1-weighted image is collected by the MRI system 100 will be described below.

(Pattern A1)

In Pattern A1, the MRI system 100 according to the exemplary embodiment includes a memory, specifying unit, and a display controller. The memory stores a corresponding color table representing correspondence relationships between T1 values of which value ranges with respect to each tissue are known and colors to be assigned to pixels with the T1 values. The specifying unit analyzes T1-weighted images and specifies colors to be assigned to each pixel on the basis of T1 values, which are converted from pixel values of each pixel, and the corresponding color table. The display controller displays on the display 24 T1-weighted images that are color-coded with the specified colors (hereinafter, "color-coded T1-weighted images" as appropriate). For example, the MRI system program/data storage 50 includes the memory and the MRI system controller 22 includes the specifying unit and the display controller (not shown).

Descriptions will be given using specific examples. The memory of the MRI system 100 stores the corresponding color table representing the corresponding relationships between T1 values and colors. For example, the memory stores a corresponding color table representing a correspondence relationship between a T1 value corresponding to a liver tissue (e.g., 586±39) and "brown", a corresponding relationship between a T1 value corresponding to a kidney cortex (e.g., 966±58) and "white", a corresponding relationship between a T1 value corresponding to a kidney medulla (e.g., 1,412±58) and "pink", and a corresponding relationship between a T1 value corresponding to a spleen (e.g., 1,057±42) and "purple". Note that the T1 values and color assignment are merely examples.

Here, the T1 values in the corresponding color table are known T1 values in value ranges for each tissue or T1 values that are actually-measured empirical values for each tissue. For example, the MRI system 100 can actually measure and accumulate value ranges of T1 values by performing various imaging under different imaging conditions and coils. For example, regarding a liver tissue, the MRI system 100 accumulates empirical T1 values to identify levels of value ranges. The memory thus stores a corresponding color table representing the correspondence relationships between such empirical T1 values and colors. The memory may previously store a corresponding color table or receive and store an entry of a correspondence relationship from an operator each time.

The MRI system 100 collects T1 weighted images. In the following exemplary embodiment, the MRI system 100 collects a plurality of T1 weighted images while changing imaging conditions (e.g., TR, TE, and pulse sequence type). For example, a plurality of T1-weighted images can be obtained such that T1 values are determined by processes in which exponentials are applied thereto. For the purpose of acquiring data necessary to calculate T1 values of each pixel, various TI (inversion time) can be used to use various TE or various IR (inversion recovery) sequences.

In other words, as understood from Table 1, because the T1 relaxation time is different for each tissue of a subject, some tissues have a higher signal intensity and some tissues have a lower signal intensity in a T1-weighted image collected under a certain imaging condition. Thus, the MRI system 100 collects a plurality of T1-weighted images while, for example, changing the imaging condition such that the signal intensity of each target tissue increases.

Figure 4:
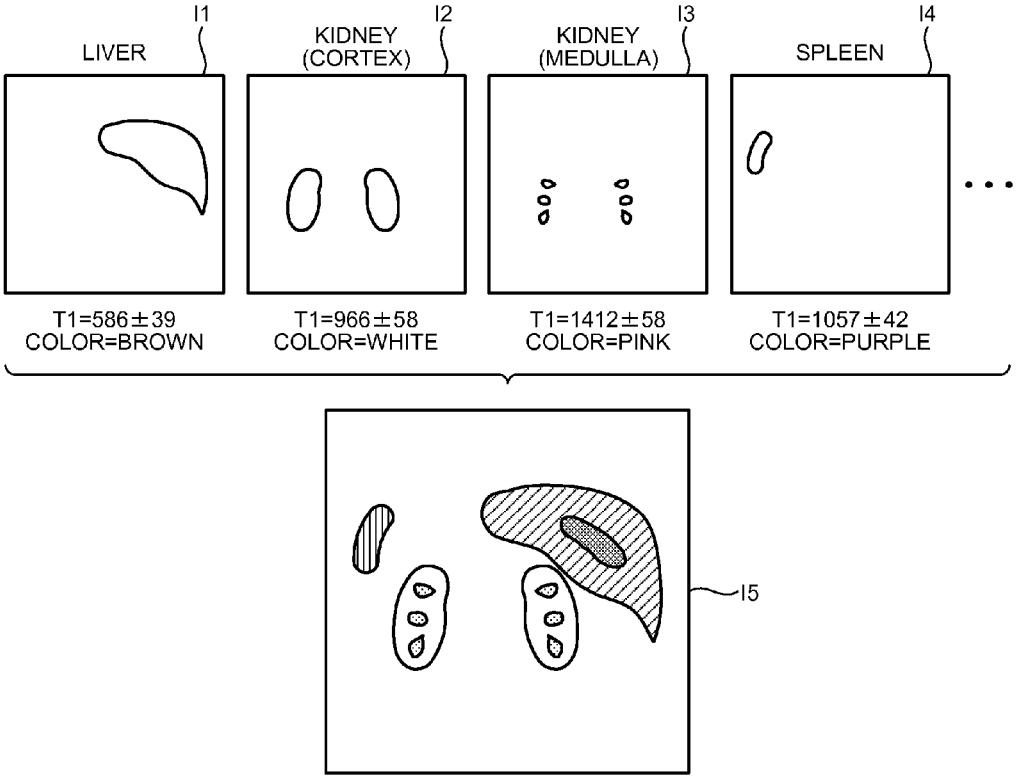
FIG. 4 is a diagram depicting exemplary screen displays of a composited T1-weighted image.

As shown in FIG. 4, for example, the MRI system 100 adjusts the imaging condition (TR, TE etc.) so as to increase the signal intensity of pixels corresponding to a liver tissue and then collects a T1-weighted image 11. For example, the MRI system 100 adjusts the imaging condition (TR, TE etc.) so as to increase the signal intensity of pixels corresponding to a kidney cortex and then collects a T1-weighted image 12. For example, the MRI system 100 adjusts the imaging condition (TR, TE etc.) so as to increase the signal intensity of pixels corresponding to a kidney medulla and then collects a T1-weighted image 13. Furthermore, for example, the MRI system 100 adjusts the imaging condition (TR, TE etc.) so as to increase the signal intensity of pixels corresponding to a spleen and then collects a T1-weighted image 14. The MRI system 100 may further collect other T1-weighted images.

In pattern A1, collecting a plurality of T1 weighted images has two purposes. One purpose is to convert pixel values to T1 values and the other purpose is to increase the signal intensity of each pixel as described above.

The specifying unit of the MRI system 100 then analyzes the T1-weighted images and converts the pixel values of each pixel to T1 values by calculation using the imaging conditions and the pixel values of the T1-weighted images. In other words, the pixel values of the T1-weighted images are defined by formulas using variables of T1 values, T2 values, and imaging conditions (Tr, Te, etc.). When the T1 values and T2 values are unknown, the specifying unit can calculate T1 values of each pixel of each T1-weighted image by solving a system of equations by using pixel values of two or more T1-weighted images.

The specifying unit refers to, using converted T1 values, a corresponding color table and specifies "colors" stored in association with the T1 values as colors to be assigned to the pixels. For example, when a converted tl value is within a range of 586±39, the specifying unit refers to the corresponding color table and specifies that the pixel is assigned "brown". In this manner, the specifying unit specifies colors to be assigned to each pixel of each T1-weighted image.

Subsequently, the display controller composites each color-coded T1-weighted image and displays the composite image on the display 24. For example, in the example of FIG. 4, the display controller generates a color-coded T1-weighted image I5 by compo siting the T1-weighted images I1 to I4 that are assigned the colors and displays the image. As shown in FIG. 4, the color-coded T1-weighted image I5 is displayed just like a schematic view. Colors may be assigned within the range so as to change, for example, from "light brown" to "dark brown" from the center value of the T1 value.

(Pattern 2)

In Pattern A2, the MRI system 100 according to the exemplary embodiment includes, as in the case of Pattern A1, a memory, a specifying unit and a display controller, and the memory further includes a corresponding value table representing correspondence relationships between pixel values of which value ranges with respect to each tissue are known and T1 values of which value ranges with respect to each tissue are known. In Pattern A2, the specifying unit converts the pixel values of each pixel to T1 values on the basis of the pixel values of each pixel and the corresponding value table.

Descriptions will be given using specific examples. The memory of the MRI system 100 further stores the corresponding value table representing correspondence relationships between pixel values and T1 values. For example, the memory stores, for each imaging condition, a corresponding value table representing corresponding relationships between pixel values and T1 values corresponding to the pixel values. For example, the MRI system 100 may actually measure correspondence relationships between pixel values and T1 values by performing various imaging using different imaging conditions or different coils. The memory thus stores correspondence tables representing correspondence relationships between pixel values and T1 values as such empirical values. The memory may previously store corresponding value tables or receive and store an entry of correspondence relationships from an operator each time.

In Pattern A2, the specifying unit performs conversion using the corresponding value tables. For example, using the pixel values of each pixel of each T1 weighted image, the specifying unit refers to the corresponding value table meeting the imaging condition and converts the pixel values to "T1 values" stored in association with the pixel values. As in Pattern A1, the specifying unit then, using the converted T1 values, refers to a corresponding color table and specifies "colors" stored in association with the T1 values as the color to be assigned to the pixels. The display controller composites each color-coded T1-weighted image and displays the image on the display 24.

In Pattern A1, a plurality of weighted images are used for two purposes: the purpose of converting pixel values to T1 values and the purpose of increasing the signal intensity of each tissue, but in Pattern A2, a plurality of T1 weighted images are not necessarily used because conversion of pixel values to T1 values is achieved by using a corresponding value table. In other words, in Pattern A2, by analyzing one T1-weighted image, a color-coded T1 weighted image may be generated and displayed.

Other examples of Pattern 2 will be described. For example, the above-described corresponding value table may represent correspondence relationships between "sample image groups of each tissue" previously collected regarding a plurality of subjects and "empirical T1 values" that are previously converted as T1 values of each sample image. In this case, the specifying unit checks a T1-weighted image, which is collected such that the signal intensity of pixels corresponding to a certain tissue is increased, against a sample image group corresponding to the tissue and obtains a correlation degree. The specifying unit then specifies a sample image with the highest correlation degree from the sample image group and, with reference to the corresponding value table, acquires a "T1 value" stored in combination with the sample image.

Subsequently, the specifying unit converts the pixel values of only pixels, from pixels contained in a T1-weighted image to be color-coded, whose signal intensity is equal to or more than a predetermined threshold to the acquired "T1 value". The specifying unit does not assign any color to pixels whose signal intensity is below the predetermined threshold. In other words, because the T1-weighted image is collected so as to increase the signal intensity of pixels corresponding to the certain tissue, the sorting using the threshold allows extraction of only the target tissue from the T1-weighted image. Thereafter, the specifying unit refers to a corresponding color table by using the converted T1 value and specifies the "color" stored in association with the T1 value as a color to be assigned to the pixels. The specifying unit then performs such a conversion process and a specifying process on each T1-weighted image corresponding to each tissue.

As in Pattern A1, the display controller then composites each color-coded T1-weighted image and displays the image on the display 24.

In the above-described Pattern A1 and Pattern A2, the examples are described in which an empirical T1 value that is actually measured is used as a T1 value of the corresponding color table or the corresponding value table, but exemplary embodiments are not limited to this. The T1 values of the corresponding color table and the corresponding value table may be "ideal T1 values".

In this case, the MRI system 100 has to have a feature to convert pixel values of each pixel to "ideal T1 values". For example, the MRI system 100 may measure and accumulate correspondence relationships between "pixel values" and "T1 values" by performing various imaging under different imaging conditions and by using different coils, It is satisfactory if, by associating the T1 values accumulated as empirical values and ideal T1 values, the MRI system 100 previously creates and stores a table representing correspondence relationships between "the pixel values" and "the ideal T1 values". In addition, it is satisfactory if, by using this table, the specifying unit converts the pixel values to "ideal T1 values".

(Pattern B)

In Pattern B, the MRI system 100 according to the exemplary embodiment includes a memory, a specifying unit and a display controller. The memory stores a corresponding color table representing correspondence relationships between pixel values corresponding to T1 values of which value ranges with respect to each tissue are known and colors to be assigned to pixels with the pixel values. The specifying unit analyzes a T1-weighted image and specifies colors to be assigned to each pixel on the basis of pixel values of each pixel and the corresponding color table. For example, the specifying unit refers to, using the pixel values of each pixel in each T1-weighted image, the corresponding color table and specifies the "colors" stored in association with the pixel values as colors to be assigned to the pixels. The display controller displays on the display 24 the T1-weighted image color-coded with the specified colors. For example, the MRI system program/data storage 50 includes the memory and the MRI system controller 22 includes the specifying unit and the display controller (not shown).

In other words, in Pattern B, on the basis of the pixel values of each pixel contained in a T1-weighted image, colors to be assigned to each pixel are specified. In this case, the corresponding color table is prepared for each imaging condition. This is because the pixel values of each pixel are different depending on the imaging condition.

The descriptions of Pattern A1, Pattern A2 and Pattern B are given above. The following various exemplary embodiments described below may be applied to the MRI system 100 in Pattern A1, Pattern A2 and Pattern B according to the exemplary embodiments.

(Other Exemplary Embodiments)

As described above, it is believed that a color-coded display of T1 values within a T1-image will make display of normal and abnormal organ/tissue signals more easily differentiated by human eyes during, for example, a diagnosis. In addition, rough ranges of T1 values expected by using IR pulses can be accumulated over time to allow even better tissue characterization (e.g., so as to differentiate cancerous tumor cells from other tissues).

This will be described in more detail, If it is assumed the horizontal axis represents the time axis and the vertical axis represents the signal intensity, the signal intensity of pixels corresponding to each tissue shifts along each different curve. In other words, the peak time varies and whether the curve is steep or gentle etc. varies in accordance with the T1 relaxation time. It is similar regarding cancerous tumor tissues. For example, it is believed that a curve along which the signal intensity of a normal tissue containing the cancerous tumor tissue changes is usually different from a curve along which the signal intensity of the cancerous tumor tissue changes. For this reason, if, for example, there is a cancerous tumor tissue in the liver, contrast between the normal tissue and the cancerous tumor tissue is not always well depicted in a T1-weighted image collected such that the signal intensity of the normal tissue in the liver is at the peak. For this reason, for example, the MRI system 100 collects and accumulates a plurality of T1-weighted images while changing the imaging condition, color-codes the images and successively displays the color-coded images on, for example, the display 24.

As shown by Table 1 representing published T1 values for various tissues (including ranges of expected variation), the MRI system 100 determines threshold ranges of T1 values so as to distinguish between various tissues. It is now proposed in the exemplary embodiment that such ranges of T1 values be color-coded (e.g., with a color for a certain range of T1 values or a color to be assigned to a particular range of T1 values). Display of such color-coded T1-weighted images will permit one to achieve better visual recognition of a target tissue even without the use of contrast agents. However, in addition, such color-coding of T1-valued images can be used in conjunction with contrast agents (e.g., which can be expected to further change the T1 values for cancerous tumor tissues, as well as normal tissues).

A plurality of T1-weighted images may be acquired so as to obtain all or any of color-coded T1-weighted images and reference images (as described below, for example, T1-weighted images not color-coded, collected T1-weighted images, or other morphological images). A range of T1 values associated with a target tissue is assigned one or more colors and the range may be used as a threshold range. For example, a first color spectrum A may be assigned to a first spectrum of T1 values. Furthermore, a second different spectrum B may be assigned to a different spectrum of T1 values (e.g., as might correspond to expected cancerous tissues that may be located within a target tissue or body area).

If injection of a contrast agent is utilized in conjunction with such color-coding of T1-weighted images, then an image display may usefully be obtained both before and after the contrast injection so that comparisons may be made between the images before and after injection of the contrast agent to enhance detection of possibly abnormal tissues.

In other words, the MRI system 100 may collect T1-weighted images without injection of any contrast agent to a subject, collect T1-weighted images while injecting a contrast agent to a subject or collect T1-weighted images before and after injection of a contrast agent. If T1-weighted images are collected before and after injection of a contrast agent, it is satisfactory if the specifying unit specifies colors by using the T1-weighted images collected before and after the injection of the contrast agent and the display controller displays on the display 24 a color-coded T1-weighted image created from the T1-weighted images before and after the injection of the contrast agent. For example, the display controller may generate color-coded T1-weighted images from the respective T1-weighted images collected before and after the injection of the contrast agent and display both of the images on the display 24. Alternatively, for example, while partly extracting pixels in which contrast of each tissue is well depicted from both of the T1-weighted images collected before and after the injection of the contrast agent, the display controller may perform compositing and display the composited color-coded T1-weighted image on the display 24.

If abnormal tissues are detected (e.g., possibly due to concentration of injected contrast agents or otherwise), then such abnormal T1-valued areas may be highlighted with a notable distinguishing color or color spectrum (e.g., a red-colored spectrum or possibly a single red color value).

The MRI system 100 configured to output such color-coded T1 image displays may provide a T1-weighted image depicting the same target area with conventional display parameters (e.g., contrast, gray scales, etc.). For example, the display controller may display a color-coded T1-weighted image superposed on a T1-weighted image before color-coding. The display controller may further display a color-coded T1-weighted image after color-coding that is superposed on a morphological image from which the morphology, such as bone, is known. In these cases, the display controller may give the color-coded T1-weighted images some transparency. In these cases, the display controller may make 2D display or 3D display. 3D display allows an observer to acquire information on the size in the depth direction of a cancerous tumor tissue in a liver tissue. It is believed that, the use of color-coded T1-weighted images provides a diagnostic tool useful for computer-aided diagnosis that correctly differentiates abnormal tissues from normal tissues based on different tissues with respectively different T1 values.

The set of color-coded T1-weighted images also can be used for CAD in conjunction with X-ray mammography and breast dynamic contrast enhancement (DCE).

The MRI system 100 can acquire a plurality of T1-weighted images (or T1 with IR pulse) to generate color-coded T1-weighted images and reference images. The MRI system 100 can then use different threshold ranges of different T1 values to make assignment of colors corresponding to different ranges of T1 values. Such threshold ranges allow the MRI system 100 to present a tissue within a normal range in one color (or spectrum of colors) and abnormal signals in a different color (or spectrum of colors). This will be described in more detail. The MRI system 100 may further include an analyzing unit that analyzes whether a pixel with a T1-value out of a predetermined range is contained in an area formed of an pixel group with T1 values within the predetermined range. In this case, when it is analyzed that a pixel with a T1 value out of the predetermined range is contained in the area, the specifying unit specifies that a first color is assigned to the pixel group with T1 values within the predetermined range and assigns a second color different from the first color to the pixel with the T1 value out of the predetermined range. For example, in such a case, it can be expected that the pixel with the T1 value out of the predetermined range is of a cancerous tumor tissue surrounded by a normal tissue. Thus, for example, the specifying unit may perform control so as to assign a color (e.g., red) previously determined as a color indicative of tissue abnormality as the second color.

Besides published data showing ranges of T1 values to be expected for different tissues, a T1 range with rough T1 values can be expected due to the measurement methods, such as imaging sequences, BO and/or B1 inhomogeneities, etc. This will be described in more detail. The "T1-valued image" includes "T1 image" and "T1-weighted image" and "T1 image" is an image of ideal values and, as described above, "T1-weighted image" is an image for which the signal intensity of the T1 value is increased. It is considered that the data on Table 1 and Table 2 is within the range of the ideal T1 value associated with each tissue of a subject. Thus, for example, The MRI system 100 can measure and accumulate ranges of T1 values by performing various imaging by using different pulse sequences or different coils. For example, for a liver tissue, empirical values representing how much by degree are accumulated.

A color-coded T1 weighted image display depicted before injection of a contrast agent may be compared to a color-coded T1-weighted image display depicted after the injection of the contrast agent to increase notice on T1 values so that a display using different colors can be made. As will be appreciated, the T1 value ranges for different abnormal tissues can be stored in databases and used as reference data for identifying particular types of tumors or cancerous tissues.

Figure 2:
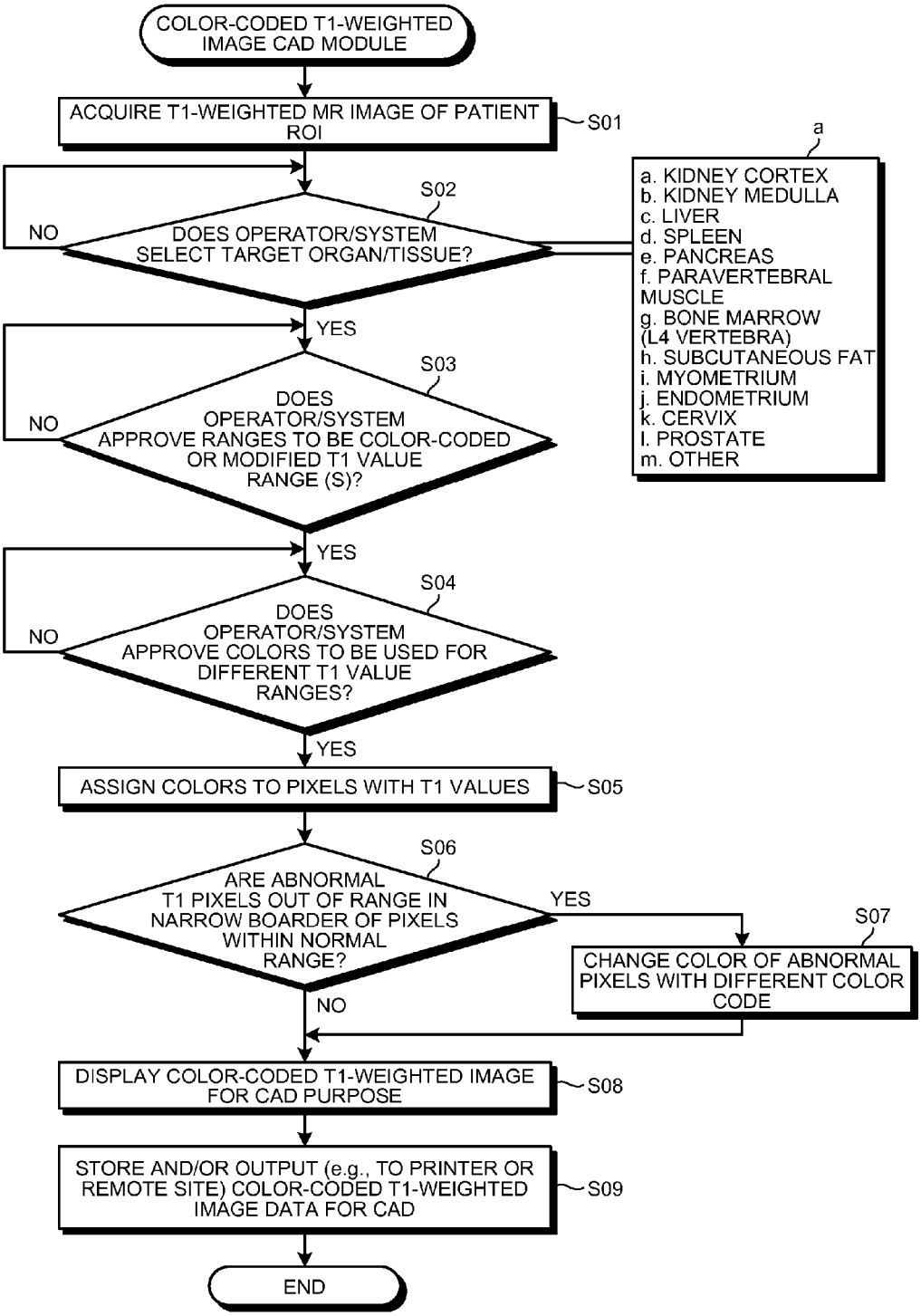
FIG. 2 is a schematic flow chart of an exemplary computer program code structure that may be utilized for practicing an exemplary embodiment.

As depicted in FIG. 2, a color-coded T1-imaged CAD module may be entered by any preferable operator-entry or system-entry mode. For example, the operator might make an operation by a mouse-selected icon, a touch-sensitive icon, a keyboard command or the like. Alternatively, the system may, in fact, select entry to this module based upon some other criteria.

At step S01, a T1-valued MR image of the region of interest (ROI) of a subject is acquired. Such a T1-valued image may be acquired by retrieving it from the memory or may be originally acquired in real time by preferable MRI data acquisition using preferable MRI sequences, calculations, etc. Accordingly, an MR image of the subject ROI having pixels with T1-values or at least T1-weighted values.

At decision box a in FIG. 2, a wait loop step S02 is started. If necessary, selection of an organ/tissue of interest can be made by an operator/system. For example, based on the entries in Table 1, the operator and/or system may have access to previously-stored expected ranges of T1 values for all or a part of many different organs and tissues of possible interest. The values of those pre-stored expected ranges may be used "as is". However, the operator/system may also have the option of modifying the ranges somewhat (e.g., so as to broaden or narrow the ranges and/or to weight the ranges in accordance with desired criteria). The operator/system may also have the option to select "other" as shown in box a. In box a, complete freedom is given to identify any desired particular range of T1 values that may be of interest for a particular target anatomy.

As already mentioned, the operator/system may have an option for approving the ranges to be color-coded or modified T1 value ranges as depicted in the optional wait loop S03 of FIG. 2.

Similarly, the operator/system may have an optional wait loop S04 as indicated in FIG. 2 for approving and/or modifying color values, spectra, etc., to be used for different T1 values and/or ranges of values. At step S05, particular color values are assigned to pixels with particular T1 values. Possibly before or after step S05, a test may be made as depicted at step S06 in FIG. 2 for pixels with abnormal T1 values out of the range (e.g., possibly being bounded by pixels with values within normal ranges). If such abnormal collections of T1-valued pixels are discovered (YES at step S06), as depicted at S07, a different color (or color spectra) code may be assigned to such abnormal pixels.

As depicted at step S08 in FIG. 2, the color-coded T1-weighted image is displayed for, for example, CAD purposes. The color-coded T1-weighted image may also be stored and/or output (e.g., to a printer or remote site) as depicted at step S09 in FIG. 2 before exit from this module.

Figure 3:
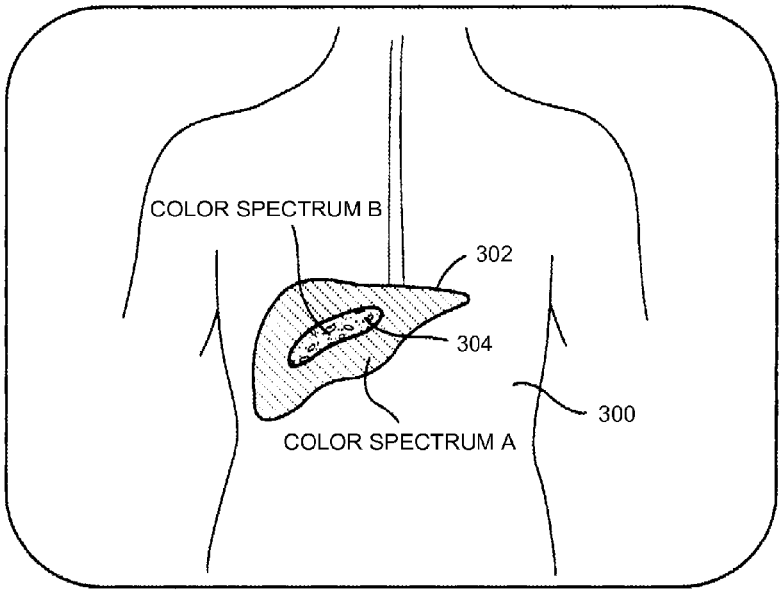
FIG. 3 is an illustration of an exemplary screen display of a T1 image showing an organ displayed with two distinguishable colors.

As a result of the module in FIG. 2, a view may be displayed as is schematically depicted at FIG. 3. Here, within the anatomy of a subject 300, an organ 302 is assigned a color spectrum A and depicted with pixels with T1 values expected to be normal. However, within the boundaries of the organ 302, pixels with unexpected, abnormal values are discovered in an area 304 and assigned a different contrasting color spectrum B. As explained previously, the system may be configured so as to permit the operator/system to assign different color spectra to pixels with T1 values within different ranges so as to optimize a CAD display for particular applications.

While the example is described above in which the MRI system 100 according to the exemplary embodiments includes the memory, the specifying unit and the display controller, exemplary embodiments are not limited to this and an image display apparatus may include a memory, a specifying unit, and a display controller. The image display apparatus may be, for example, a personal computer or a work station. In this case, the memory of the image display apparatus stores a corresponding color table representing correspondence relationships between T1 values of which value ranges with respect to each tissue are known and colors to be assigned to pixels with the T1 values. The specifying unit analyzes a T1-valued image and specifies colors to be assigned to each pixel on the basis of T1 values converted from the pixel values of each pixel and the corresponding color table. The display controller displays on the display an image color-coded with the specified colors. Alternatively, the memory of the image display apparatus stores a corresponding color table representing correspondence relationships between pixel values corresponding to T1 values of which value ranges for each pixel are known and colors to be assigned to pixels with the pixel values. The specifying unit analyzes a T1-valued image and specifies colors to be assigned to each pixel on the basis of the pixel values of each pixel and the corresponding color table. The display controller displays on the display an image color-coded with the specified colors. The memory is, for example, a memory and the specifying unit and the display controller are, for example, processors.

The MRI system 100 according to the exemplary embodiments may use only a real part of complex number without imaginary part of complex number when reconstructing a T1-weighted image. Analysis using only the real part allows the MRI system 100 to obtain accurate T1 values from its obliqueness.

The magnetic resonance imaging apparatus, the magnetic resonance imaging method and the image display apparatus according to at least one of the above-described exemplary embodiments can display MR images appropriately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:

MRI gantry components including static and gradient magnetic field generators, at least one radio frequency (RF) coil coupled to an imaging volume, at least one RF transmitter, at least one RF receiver and at least one control computer having at least one processor and memory configured to control said gantry components to collect a plurality of T1-valued images in which signal intensity of a distinct target tissue in each image is increased relative to non-target tissues;

the memory configured to store a color table representing correspondence relationships between (A) ranges of known T1 values with respect to each tissue and (B) colors to be assigned to pixels with the known T1 values;

the at least one processor configured to analyze the plurality of T1-valued images and to specify colors to be assigned to each pixel of each of the plurality of T1-valued images on the basis of (a) T1 values, converted from pixel values of each pixel, and said color table; and the at least one processor configured to display on a display the plurality of T1-valued images color-coded with the specified colors.

2. The magnetic resonance imaging apparatus according to claim 1, wherein:

the gantry components collect the plurality of T1-valued images in which signal intensity of the distinct target tissue in each image is increased relative to non-target tissues by imaging under different imaging conditions, and the plurality of T1-valued images are analyzed by the at least one processor by converting pixel values of each pixel to T1 values by calculations using (i) the imaging conditions and (ii) pixel values of the images.

3. The magnetic resonance imaging apparatus according to claim 1, wherein:

the memory further stores a value table representing correspondence relationships between (C) pixel values of which value ranges with respect to each tissue are known and (A) T1 values of which value ranges with respect to each tissue are known; and pixel values of each pixel of the plurality of T1-valued images are converted by the at least one processor to T1 values on the basis of (i) the pixel values of each pixel and (ii) said value table.

4. The magnetic resonance imaging apparatus according to claim 1, wherein:

the gantry components collect the plurality of T1-valued images in which signal intensity of the distinct target tissue in each image is increased relative to non-target tissues by imaging under different imaging conditions, and each of said color-coded images are composited together by the at least one processor and displayed as a resulting color-coded composite image on the display.

5. The magnetic resonance imaging apparatus according to claim 1, wherein, in accordance with the plurality of T1-valued images, the at least one processor determines whether a pixel with a T1 value outside of a predetermined range is contained within an area formed of a pixel group with T1 values within the predetermined range, wherein, when it is analyzed that a pixel with a T1 value outside of the predetermined range is contained within the area, the specifying unit (a) specifies that a first color is assigned to the pixel group with the T1 values within the predetermined range and (b) specifies that a second color, different from the first color, is assigned to the pixel with the T1 value outside of the predetermined range.

6. The magnetic resonance imaging apparatus according to claim 5, wherein the specifying unit assigns a predetermined color as the second color.

7. The magnetic resonance imaging apparatus according to claim 1, wherein at least one of the T1-valued images is an image collected without contrast agent having been injected into a subject.

8. The magnetic resonance imaging apparatus according to claim 1, wherein at least one of the T1-valued images is an image collected while an injected contrast agent is present in a subject.

9. The magnetic resonance imaging apparatus according to claim 1, wherein:

the plurality of T1-valued images include a first image collected before a contrast agent is injected to a subject and a second image collected after the contrast agent is injected, and the display controller simultaneously displays on the display both the first image and the second image that are color-coded.

10. The magnetic resonance imaging apparatus according to claim 1, wherein the display controller displays the color-coded images superimposed on a non-color-coded morphological image of the same patient anatomy.

11. The magnetic resonance imaging apparatus according to claim 1, wherein the T1 values are (a) ideal T1 values associated with each tissue of a subject or (b) actually-measured empirical T1 values associated with each tissue of the subject.

12. A magnetic resonance imaging apparatus comprising:

MRI gantry components including static and gradient magnetic field generators, at least one radio frequency (RF) coil coupled to an imaging volume, at least one RF transmitter, at least one RF receiver and at least one control computer having at least one processor and memory configured to control said gantry components to collect a plurality of T1-valued images in which signal intensity of a distinct target tissue in each image is increased relative to non-target tissues;

the memory configured to store a color table representing correspondence relationships between (A) pixel values corresponding to ranges of known T1 values with respect to each tissue and (B) colors to be assigned to pixels with the pixel values;

the at least one processor configured to analyze the plurality of T1-valued images and to specify colors to be assigned to each pixel of each of the plurality of T1-valued images on the basis of (a) pixel values of each pixel and (b) said color table; and the at least one processor configured to display on a display the plurality of T1-valued images color-coded with the specified colors.

13. A magnetic resonance imaging method performed by a magnetic resonance imaging (MRI) apparatus including a memory configured to store a color table representing correspondence relationships between (A) ranges of known T1 values with respect to each tissue and (B) colors to be assigned to pixels with the known T1 values, the method comprising:

collecting, with the MRI apparatus, a plurality of T1-valued images in which signal intensity of a distinct target tissue in each image is increased relative to non-target tissues;

analyzing the plurality of T1-valued images and specifying colors to be assigned to each pixel of each of the plurality of T1-valued images on the basis of (a) T1 values, converted from pixel values of each pixel, and (b) said color table; and displaying on a display the plurality of T-1 valued images color-coded with the specified colors.

14. A magnetic resonance imaging method performed by a magnetic resonance imaging (MRI) apparatus including a memory configured to store a color table representing correspondence relationships between (A) pixel values corresponding to ranges of known T1 values with respect to each tissue and (B) colors to be assigned to pixels with the pixel values, the method comprising:

collecting, with the MRI apparatus, a plurality of T1-valued images in which signal intensity of a distinct target tissue in each image is increased relative to non-target tissues;

analyzing the plurality of T1-valued images and specifying colors to be assigned to each pixel of each of the plurality of T1-valued images on the basis of (a) pixel values of each pixel and (b) said color table; and displaying on a display the plurality of T-1 valued images color-coded with the specified colors.

15. A magnetic resonance image display apparatus comprising:

at least one processor and memory configured to store a color table representing correspondence relationships between (A) ranges of known T1 values with respect to each tissue and (B) colors to be assigned to pixels with the known T1 values;

the at least one processor configured to analyze a plurality of T1-valued images in which signal intensity of a distinct target tissue in each image has been increased relative to non-target tissues by an MRI signal acquisition process, and specifies colors to be assigned to each pixel of each of the plurality of T1 valued images on the basis of (a) T1 values converted from pixel values of each pixel and (b) said color table; and the at least one processor configured to display on a display the plurality of T1-valued images color-coded with the specified colors.

16. A magnetic resonance image display apparatus comprising:

*at least one processor and* a memory configured to store a color table representing correspondence relationships between (A) pixel values corresponding to ranges of known T1 values with respect to each tissue and (B) colors to be assigned to pixels with the pixel values;

the at least one processor configured to analyze a plurality of T1-valued images in which signal intensity of a distinct target tissue in each image has been increased relative to non-target tissues by an MRI signal acquisition process, and to specify colors to be assigned to each pixel of each of the plurality of T1-valued images on the basis of (a) pixel values of each pixel and (b) said color table; and the at least one processor configured to display on a display the plurality of T1-valued images color-coded with the specified colors.

*17. An image processing apparatus comprising:*

*a memory configured to accumulate and store value tables representing correspondence relationships between signal intensities of pixels of an MR image and quantitative values, wherein the value tables are actually measured by performing various imagings using different imaging conditions; and*

*a programmed processor connected to communicate with said memory and configured to refer to a value table corresponding to imaging conditions of pixels of an MR image obtained by imaging, obtain a quantitative value corresponding to a signal intensity of each pixel of the MR image, and display on a display an image color-coded with colors corresponding to the determined quantitative values.*

*18. The image processing apparatus according to claim 17, wherein*

*the memory is further configured to store a color table representing correspondence relationships between ranges of quantitative values and specific colors, each range of quantitative values corresponding to a specific tissue, and*

*the processor displays the image being color-coded based on the color table.*

*19. The image processing apparatus according to claim 17, wherein the quantitative value is at least one of a T1 value and a T2 value.*

*20. A magnetic resonance imaging apparatus comprising:*

*MRI gantry components including static and gradient magnetic field generators, at least one radio frequency (RF) coil coupled to an imaging volume, at least one RF transmitter, at least one RF receiver and at least one control computer having at least one programmed processor and memory configured to control said gantry components;*

*the memory being configured to accumulate and store value tables representing correspondence relationships between signal intensities of pixels of an MR image and quantitative values, wherein the value tables are actually measured by performing various imagings using different imaging conditions; and*

*the at least one programmed processor being connected to communicate with said memory and configured to refer to a value table corresponding to imaging conditions of an MR image obtained by imaging, obtain a quantitative value corresponding to a signal intensity of each pixel of the MR image, and display on a display an image color-coded with colors corresponding to the determined quantitative values.*

*21. The magnetic resonance imaging apparatus according to claim 20, wherein*

*the memory is further configured to store a color table representing correspondence relationships between ranges of quantitative values and specific colors, each range of quantitative values corresponding to a specific tissue, and*

*the processor displays the image being color-coded based on the color table.*

*22. The magnetic resonance imaging apparatus according to claim 20, wherein the quantitative value is at least one of a T1 value and a T2 value.*

*23. An image processing method comprising:*

*using a programmed computer connected for communication with a data memory to:*

*refer to a value table corresponding to imaging conditions of an MR image obtained by imaging, wherein the value table is stored in the memory configured to accumulate and store value tables representing correspondence relationships between signal intensities of pixels of an MR image and quantitative values, wherein the value tables are actually measured by performing various imagings using different imaging conditions;*

*obtain a quantitative value corresponding to a signal intensity of each pixel of the MR image; and*

*display on a display an image color-coded with colors corresponding to the determined quantitative values.*

*24. The image processing method according to claim 23, wherein*

*the image displayed on the display is color-coded based on a color table that is stored in the memory and that represents correspondence relationships between ranges of quantitative values and specific colors, each range of quantitative values corresponding to a specific tissue.*

*25. The image processing method according to claim 23, wherein the quantitative value is at least one of a T1 value and a T2 value.*

* * * * *